(12) United States Patent
Howlett

(10) Patent No.: US 6,336,455 B1
(45) Date of Patent: Jan. 8, 2002

(54) RELATING TO DISPENSING APPARATUS

(75) Inventor: David Howlett, King's Lynn (GB)

(73) Assignee: Bespak PLC, Norfolk (GB)

(*) Notice: Subject to any disclaimer, the term of this patent is extended or adjusted under 35 U.S.C. 154(b) by 0 days.

(21) Appl. No.: 09/458,046

(22) Filed: Dec. 10, 1999

(30) Foreign Application Priority Data

Dec. 11, 1998 (GB) .............................................. 9827402

(51) Int. Cl.[7] .............................................. A61M 15/00
(52) U.S. Cl. .............................. 128/203.15; 128/200.23
(58) Field of Search ....................... 128/203.15, 203.12, 128/203.18, 203.19, 203.21, 200.14, 200.17, 200.18, 200.22, 200.23; 604/58

(56) References Cited

U.S. PATENT DOCUMENTS

| | | | | |
|---|---|---|---|---|
| 2,534,636 A | * | 12/1950 | Stirn | 128/203.15 |
| 4,452,239 A | * | 6/1984 | Malem | 128/200.17 |
| 5,165,391 A | * | 11/1992 | Chiesi et al. | 128/200.23 |
| 5,284,133 A | * | 2/1994 | Burns et al. | 128/200.23 |
| 5,309,900 A | | 5/1994 | Knoch et al. | |
| 5,318,016 A | * | 6/1994 | Mecikalski | 128/200.23 |
| 5,435,301 A | * | 7/1995 | Herold et al. | 128/203.15 |
| 5,596,982 A | * | 1/1997 | Blaha-Schnabel | 128/200.14 |
| 5,622,163 A | * | 4/1997 | Jewett et al. | 128/200.23 |
| 5,775,320 A | * | 7/1998 | Patton et al. | 128/200.14 |
| 5,875,776 A | * | 3/1999 | Vaghefi | 12/203.15 |
| 6,073,629 A | * | 6/2000 | Hardy et al. | 128/203.15 |
| 6,089,227 A | * | 7/2000 | Nilsson | 128/203.15 |
| 6,148,815 A | * | 11/2000 | Wolf | 128/205.23 |
| 6,230,707 B1 | * | 5/2001 | Horlin | 128/203.15 |

FOREIGN PATENT DOCUMENTS

| | | |
|---|---|---|
| EP | 0 475 257 | 3/1992 |
| WO | WO 88/03419 | 5/1988 |
| WO | WO 90/15635 | 12/1990 |
| WO | WO 98/26827 | 6/1998 |

* cited by examiner

Primary Examiner—John G. Weiss
Assistant Examiner—Teena Mitchell
(74) Attorney, Agent, or Firm—Smith, Gambrell & Russell LLP

(57) ABSTRACT

The present invention relates to an inhalation apparatus for dispensing substances for inhalation and, in particular, but not exclusively for dispensing medicinal products. An inhalation apparatus is provided having a housing defining a socket for receiving a pressurized dispensing container, an actuator for receiving a valve stem of the pressurized dispensing container and a cylindrical chamber having an inlet located at a periphery of the chamber and an outlet at or near a center of the chamber. The actuator defines a duct designed to direct product dispensed from the valve stem of the pressurized dispensing container through the inlet of the cylindrical chamber in a direction substantially tangential to the major axis of the cylindrical chamber, the outlet of the cylindrical chamber communicating with a mouthpiece, such that the inhalation by a user on the mouthpiece creates a cyclonic airflow in the cylindrical chamber between the inlet and outlet in which the dispensed product is entrained for inhalation.

20 Claims, 6 Drawing Sheets

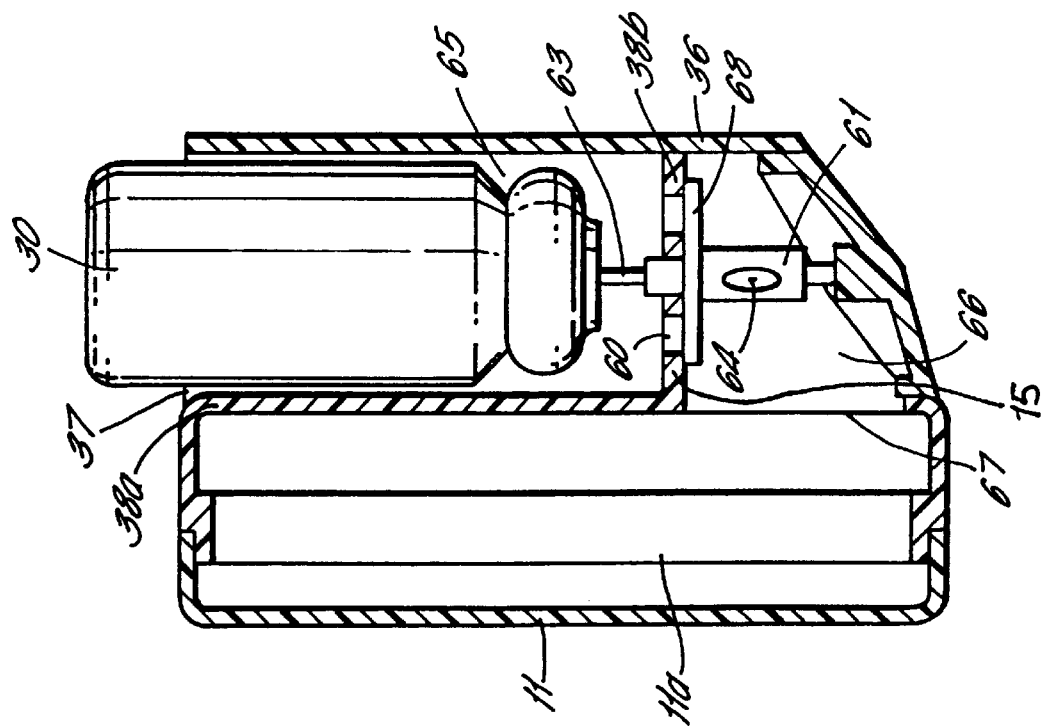
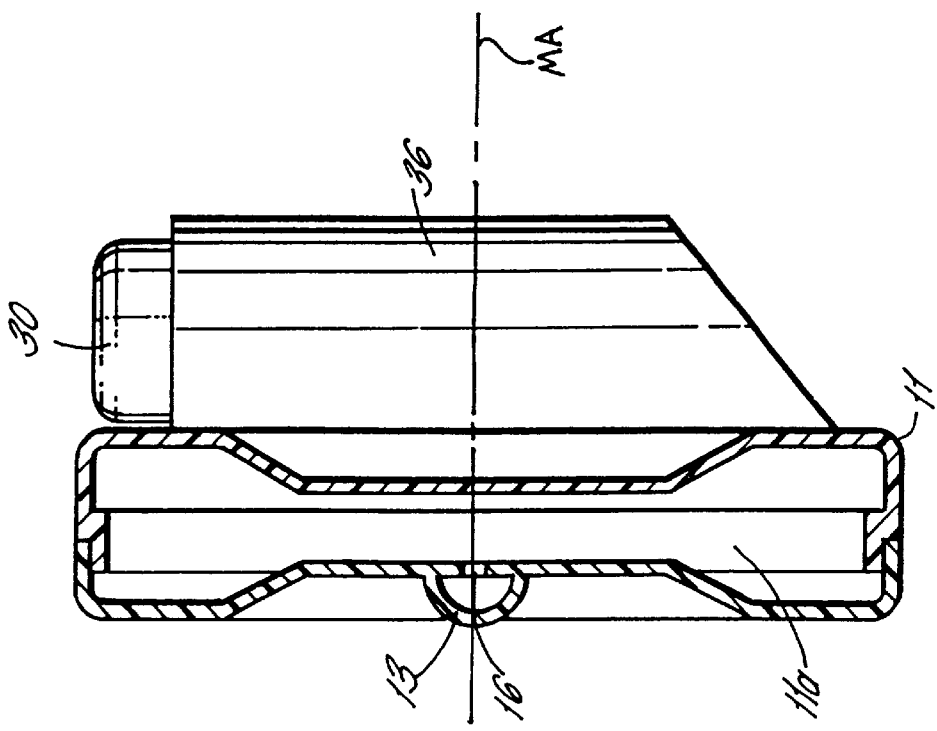

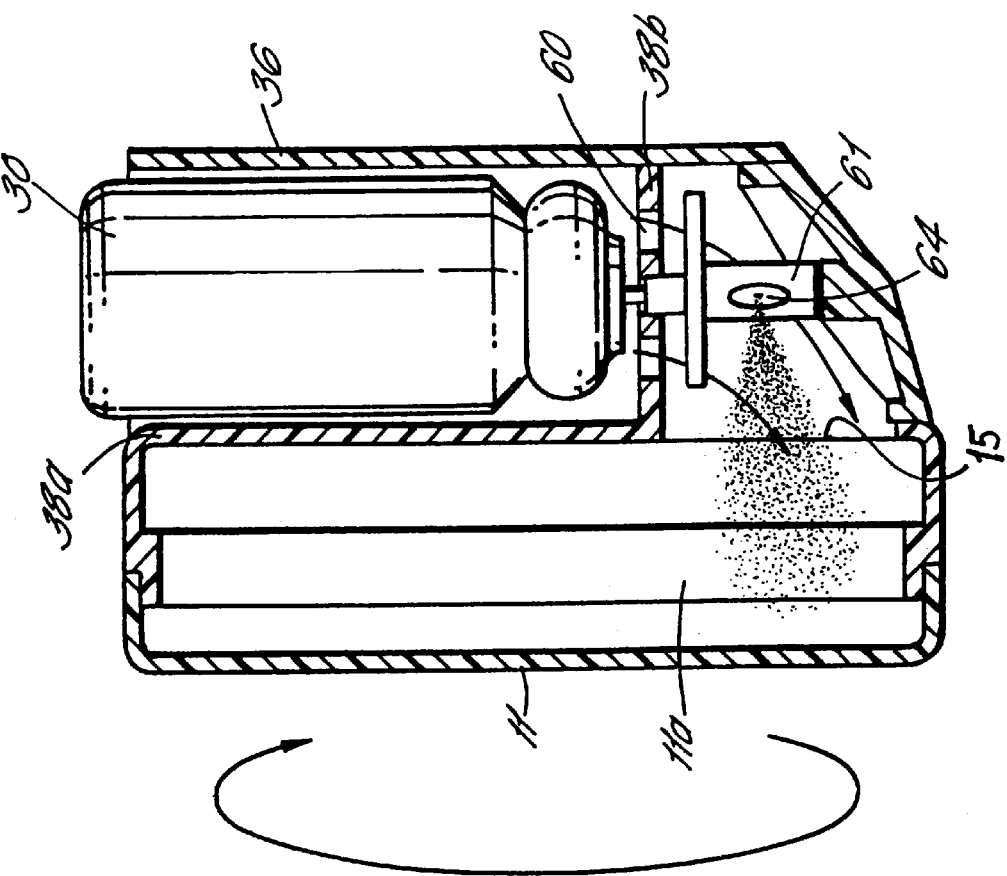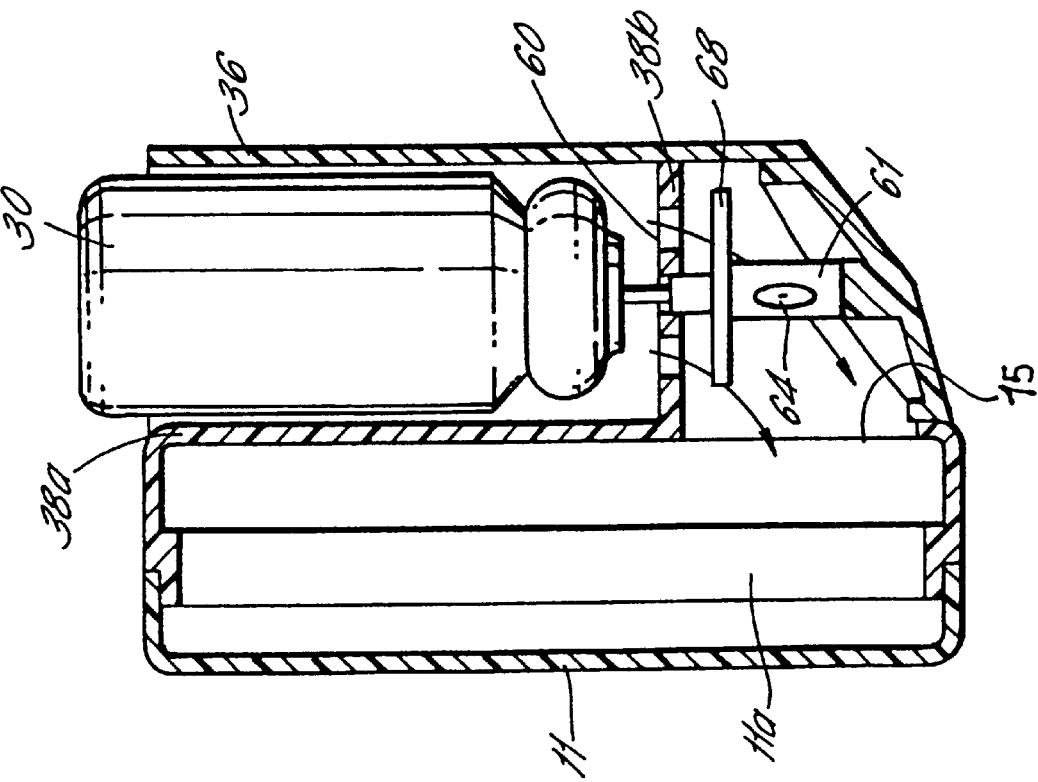

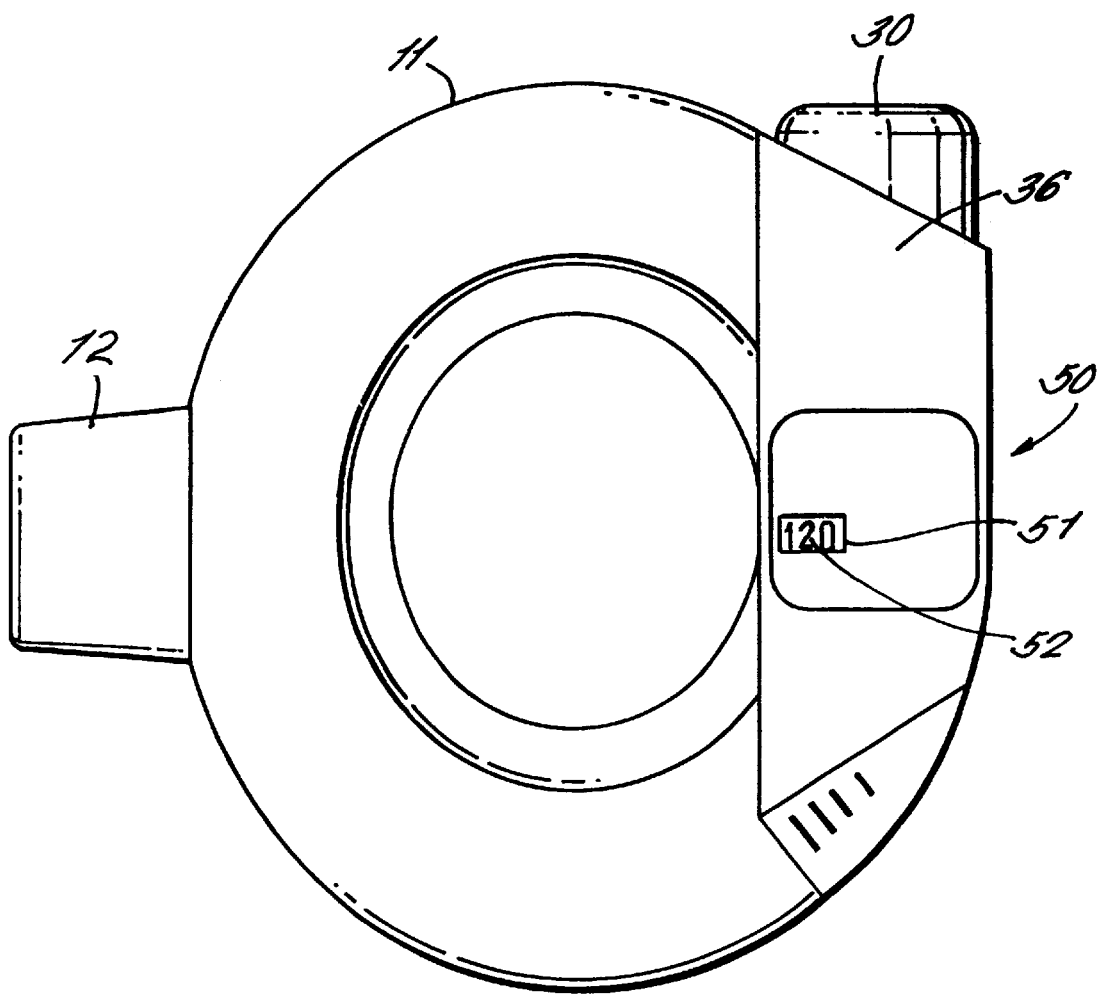

RELATING TO DISPENSING APPARATUS

FIELD OF THE INVENTION

This invention relates to an inhalation apparatus for dispensing substances for inhalation and, in particular, but not exclusively, for dispensing medicinal products.

BACKGROUND OF THE INVENTION

Known dispensing apparatus for use in inhalation apparatus include metered dose inhalers and dry powder inhalers. In known metered dose inhalers, the aerosol stream from a pressurized dispensing container is fired towards a patient or user of the inhaler into an airflow travelling in the same direction. A user inhales through a mouthpiece of the inhaler and creates an airflow through the container from air inlet holes which are generally at a part of the inhaler well spaced from the mouthpiece. Medicament is then released into this airflow at a point between the air inlet holes and the mouthpiece so that it is travelling in the same direction as the airflow. Typically, in such devices, there is no restriction in the airflow between the air inlet holes and the mouthpiece. Because of this, a substantial airflow can be created by the user of the device and, because the medicament is fired into the airflow in the same direction as the airflow, the effect is that particles of medicament can attain quite substantial velocities. As inhalers of this type are normally designed to be as small as practical for the convenience of the user, the distance between the point at which the medicament is fired and the patient's mouth is usually quite small so that there is little distance for the inertia of the particles of medicament to decrease with the result that the particles may impact in the oropharynx of a user with quite high velocity. This can be a problem with certain medicaments.

In known dry powder inhalers, powdered medicament, which is often combined with a powdered carrier, such as lactose, is stored within a delivery device until delivery of the medicament is required. It is known to store the medicament in a bulk holding reservoir in the delivery device. The drug is removed from the reservoir on an as required basis. It is also known to provide dry powder inhalers wherein the medicament is contained within discrete doses within a dosage unit such as a gelatine capsule. A problem with both types of known dry powder inhaler is that the medicament and carrier can form relatively large particles which when inhaled by the user do not reach deep into the lungs, which has been shown to be necessary for the most advantageous medical result to be obtained. It is known to provide baffle plates within an airflow passageway of a dry powder inhaler such that the medicament and carrier impact on the baffle plates and are, to a degree, separated and the particle size reduced. However, a problem with such baffle plates is that the medicament and carrier only pass through the baffle plates once and, as a result, a significant proportion of larger particles still exit the inhaler and are inhaled by the user.

BRIEF SUMMARY OF THE INVENTION

According to the present invention there is provided inhalation apparatus comprising a housing defining a socket for receiving a pressurized dispensing container, actuator means for receiving a valve stem of the pressurized dispensing container and a cylindrical chamber having an inlet located at a periphery of the chamber and an outlet at or near a center of the chamber, the actuator means defining duct means to direct product dispensed from the valve stem of the pressurized dispensing container through the inlet of the cylindrical chamber in a direction substantially tangential to the major axis of the cylindrical chamber, the outlet of the cylindrical chamber communicating with a mouthpiece, such that inhalation by a user on the mouthpiece creates a cyclonic airflow in the cylindrical chamber between the inlet and outlet in which the dispensed product is entrained for inhalation.

The present invention also provides a method of inhaling product dispensed from a pressurized dispensing container comprising the steps of inhaling on a mouthpiece of an inhalation apparatus comprising a cylindrical chamber having an inlet at a periphery thereof and an outlet at or near a center thereof which communicates with the mouthpiece, to thereby create a cyclonic airflow from the inlet to the outlet, actuating the pressurized dispensing container to dispense a dose of product through the inlet of the cylindrical chamber in a direction substantially tangential to the major axis of the cylindrical chamber such that the product is entrained in the airflow and inhaled through the mouthpiece.

BRIEF DESCRIPTION OF THE FIGURES

Preferred embodiments of the present invention will now be described, by way of example only, with reference to the accompanying drawings, in which:

FIG. 3 is a cross-sectional elevation taken on line III—III of FIG. 1;

FIG. 4 is a schematic cross-section taken on line IV—IV of FIG. 1;

FIG. 5 shows the apparatus of FIG. 4 immediately prior to dispensing of medicament;

FIG. 6 shows the apparatus of FIG. 4 during dispensation of medicament;

FIG. 7 shows a side elevation of a second embodiment of dispensing apparatus according to the present invention;

DETAILED DESCRIPTION OF THE INVENTION

Figure 2:
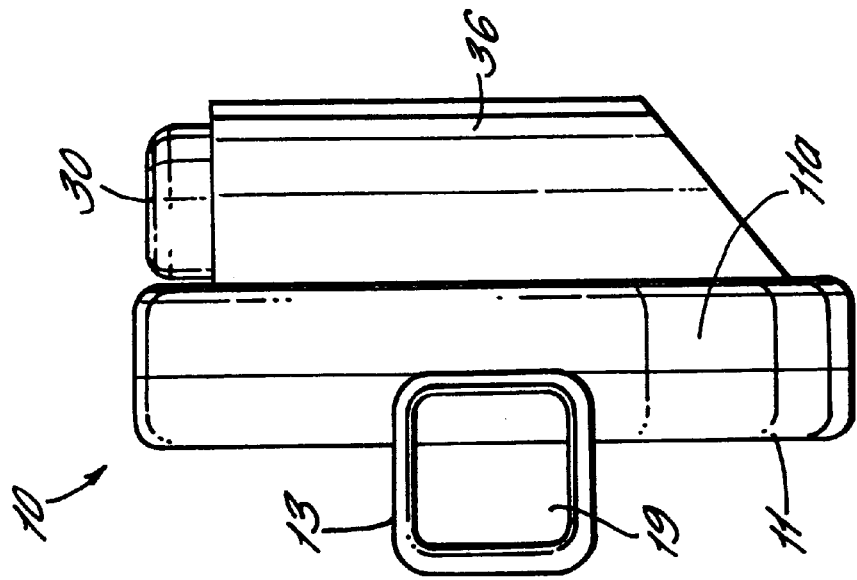
FIG. 2 is a front elevation of the apparatus of FIG. 1.
Figure 1:
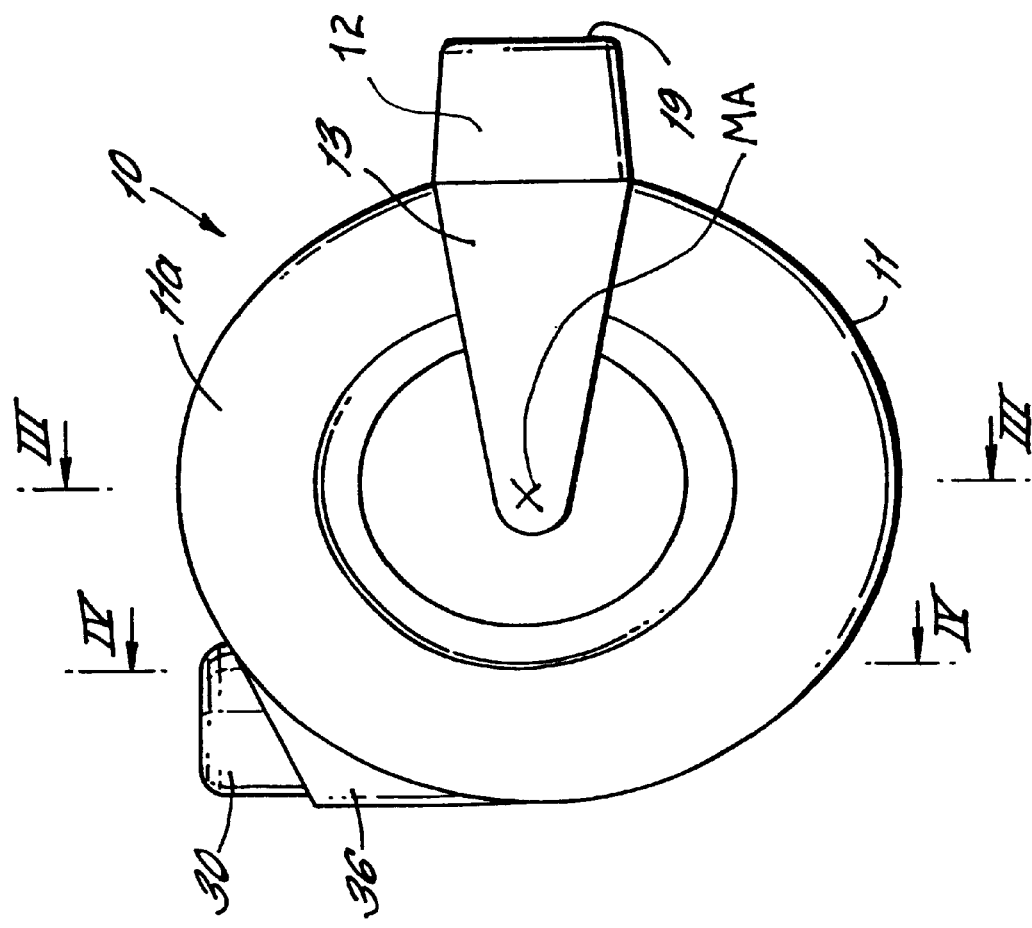
FIG. 1 is a side elevation of a first embodiment of dispensing apparatus according to the present invention.

The dispensing apparatus of the present invention as shown in FIGS. 1 to 9 comprises a spacer unit generally denoted by reference 10 which is either permanently or releasably connected in use to a dispensing unit generally designated by reference numeral 30.

In the illustrated embodiments, dispensing unit 30 comprises a pressurized dispensing container of the type consisting of a pressurized container, metering valve attached thereto having a valve stem 63 extending axially to protrude from the metering valve. The illustrated dispensing unit or pressurized dispensing container 30 typically contains medicament either in solution or suspension and a propellant system.

The spacer unit 10 of the first embodiment as shown in FIGS. 1 to 6 comprises a generally cylindrical housing 11 defining a spacer chamber 11a. The spacer chamber 11a has a major axis "MA" aligned with a center of housing 11.

A hollow mouthpiece duct 13 extends radially outwardly from the center of the housing 11 terminating in a substantially tubular mouthpiece 12 which extends beyond the periphery of the housing 11. The mouthpiece 12 defines an outlet 19. The spacer chamber 11a communicates with the mouthpiece duct 13 through an aperture 16 in one side of the housing 11 positioned at or near the center as best shown in FIG. 3.

Preferably, the width of the chamber 11a, as measured in the direction of the major axis, decreases from the periphery of the chamber 11a to the center.

The housing 11, inlet duct 15 and mouthpiece duct 13 may all be moulded from suitable plastics materials and are preferably moulded as a single unit.

A generally cylindrical housing 36 is integrally formed on one side of housing 11. As shown in FIG. 4, the cylindrical housing 36 is divided into upper and lower sections 65 and 66 by an annular partition 38b. Airflow holes 60 are provided in the partition to allow air to pass from the upper to lower section. The upper section 65 of the cylindrical housing 36 defines a socket 37, in which in use the pressurized dispensing container 30 is inserted, and is separated from spacer chamber 11a by a partition 38a. The pressurized dispensing container 30 fits loosely in the upper section 65 of the cylindrical housing 36 such that air may readily pass between the pressurized dispensing container 30 and the walls of the cylindrical housing.

The lower section 66 of the cylindrical housing 36 communicates with the spacer chamber 11a through an aperture 67 which opens into the chamber 11a tangentially.

The lower section 66 of the cylindrical housing 36 contains an actuator 61. the actuator 61 has a cylindrical body, in an upper end of which is a bore for receiving a valve stem of the pressurized dispensing container 30 when the pressurized dispensing container is inserted in socket 37 with the valve stem 63 lowermost. The valve stem receiving bore communicates via a duct with an opening 64 in the side wall of the actuator body which is arranged to direct aerosol through 90° on discharge in a director towards the aperture 67 connecting the lower section 66 with the spacer chamber 11a. The actuator 61 also comprises a radially extending flange 68 of a large enough diameter to sealingly cover and close the airflow holes 60. A helical compression spring is provided between a lower end of the actuator 61 and a base of the cylindrical housing to bias the actuator 61 upwardly such that, in the rest position, the annular flange 68 contacts the partition 38b and seals the airflow holes 60.

In use, the user inserts the mouthpiece 12 of the spacer unit 10 into their mouth and inhales. Initially, as the airflow holes 60 are sealed by the flange 68, there is no airflow. Whilst continuing to inhale, the user manually depresses the dispensing container 30 causing the valve stem 63 to move downwardly. In turn, this causes the actuator 61 to slide axially downwards and compress the spring. The flange 68 of the actuator 61 is thus moved out of contact with the airflow holes 60 allowing the passage of air from an exterior of the device through the upper section 65 between the pressurized dispensing container 30 and walls, through the airflow holes 60, lower section 66 and aperture 67 into spacer chamber 11a.

The airflow entering the spacer chamber 11a enters in a direction having a substantial tangential component relative to the major axis such that the airflow is constrained to move in a rotational manner around the spacer chamber 11a due to the cylindrical shape of housing 11. As the user inhales air is drawn towards the center of the spacer chamber 11a and out through aperture 16, along mouthpiece duct 13 and exists outlet 19 where it is inhaled by the user. Thus, inhalation by the user creates a cyclonic, rotating air flow within spacer chamber 11a. The product when entrained in the air flow passes with the air into spacer chamber 11a. Due to the cyclonic nature of the air flow within spacer chamber 11a, larger particles of the product are held in the peripheral region of the spacer chamber 11 whilst smaller particles are drawn towards the center of the spacer chamber 11a where they exit the chamber 11a through aperture 16 into mouthpiece duct 13 and mouthpiece 12 where they are inhaled. Thus, the cyclonic air flow in chamber 11a acts on the medicament as a classifier separating the relatively small particles from relatively large particles and only passing relatively small particles through aperture 16 for inhalation.

Further depression of the dispensing container 30 causes the lower end of the actuator 61 to come into contact with the base of the cylindrical housing at which point further axial movement of the actuator 61 is prevented. Thus, the valve stem 63 is depressed inwardly relative to the metering valve of the pressurized dispensing container 30 and a dose of product is discharged as a fine aerosol mist which is then entrained in the airflow.

The cyclonic flow of the entrained aerosol acts to classify the aerosol as described above. Larger aerosol droplets are held in the periphery of the spacer chamber 11a and only the relatively smaller aerosol droplets are drawn to the center and exit through aperture 16 for inhalation. This has the beneficial effect that smaller aerosol droplets are able to be inhaled deeper into the lungs than larger droplets. This has been found to have beneficial medical results, especially for medicaments for treating respiratory disorders such as asthma. The cyclonic nature of the flow also results in the flow path length of the aerosol being greatly increased when compared to a linear spacer. The airflow and entrained aerosol pass round the spacer chamber 11a many times before existing through aperture 16. This provides a greatly increased time for the speed and inertia of the aerosol droplets to decrease before they are delivered to the user. As a result there is a greatly reduced risk of the aerosol droplets forcibly impacting on the oro-pharynx region of the throat of the user with its associated discomfort and potential damage.

It should be noted that this embodiment is suitable for use with many types of dispensing unit in which actuation of the pressurized dispensing container is coordinated with the inhalation cycle of the user and is not restricted to the particular device herein described.

FIG. 7 shows a second embodiment of dispensing apparatus according to the present invention. The dispensing unit 30 and spacer unit 10 are the same as those described in the first embodiment. However, in addition, the dispensing apparatus is provided with a counter module 50 comprising a dose counting mechanism linked to the dispensing unit 30. A counter window 51 is provided viewable from an exterior of the housing 11 through which is displayed in use a counter indication 52 indicating either the number of doses dispensed or the number of doses remaining to be dispensed. The counter module is linked to the dispensing unit 30 such that each actuation of the dispensing unit actuates the counter module to either increment or decrement the counter indication as appropriate.

Figure 8:
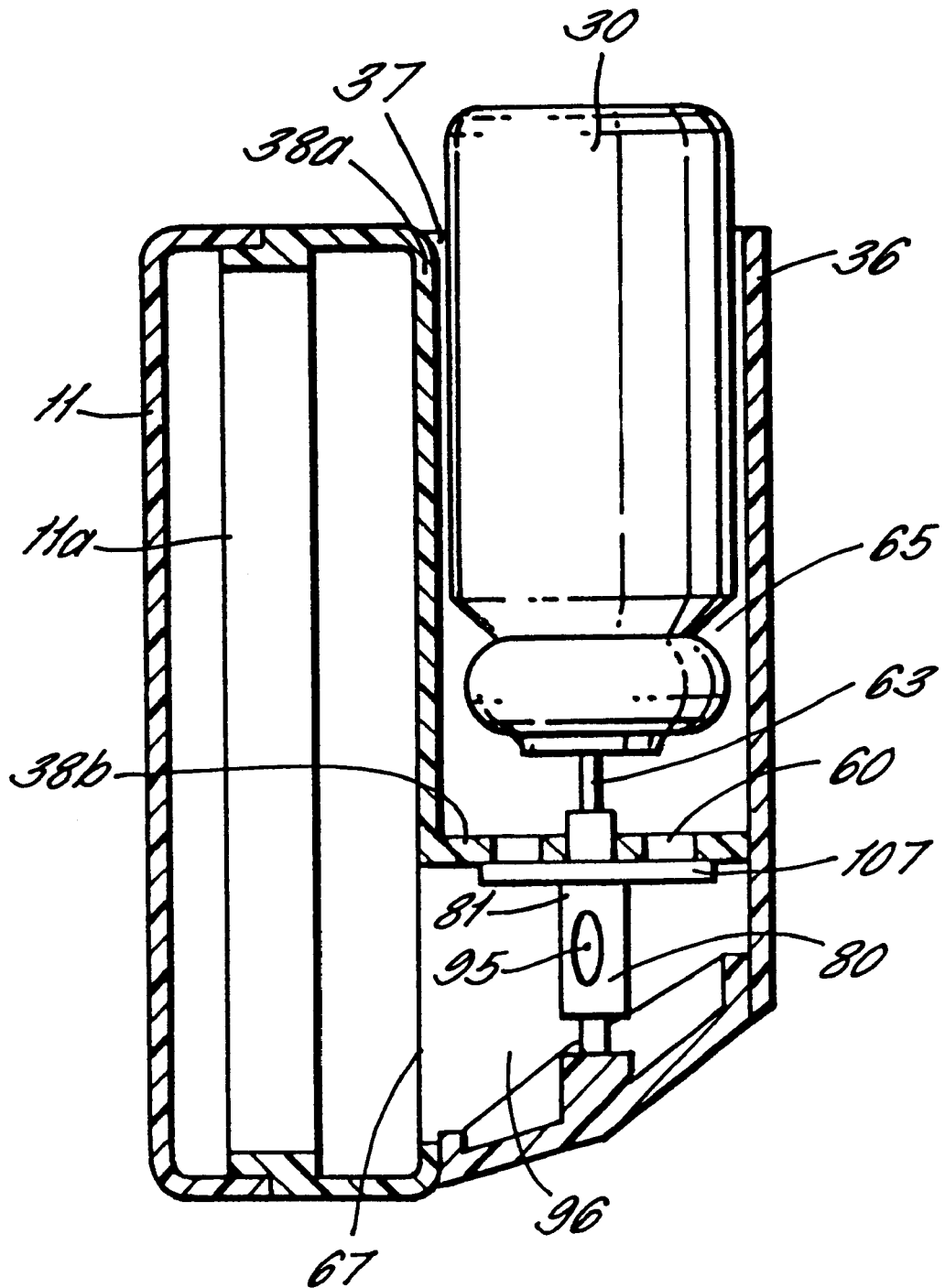
FIG. 8 shows a cross-sectional schematic elevation of a third embodiment of dispensing apparatus according to the present invention.
Figure 9:
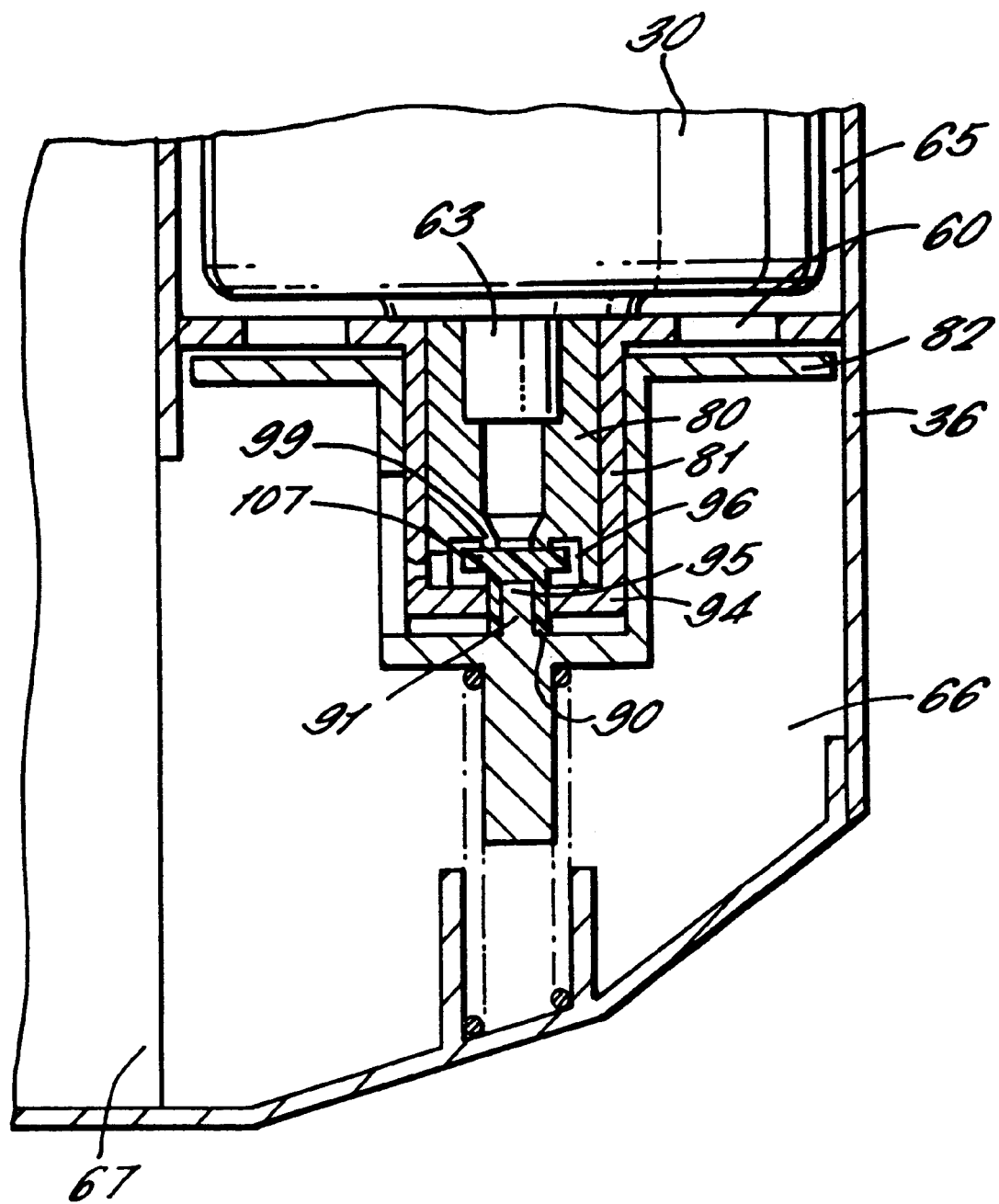
FIG. 9 shows a enlarged cross-sectional schematic elevation of part of the apparatus of FIG. 8.

FIGS. 8 and 9 show a third embodiment of dispensing apparatus according to the present invention. The dispensing unit 30 is a pressurized dispensing container and is identical to that described in the first embodiment. The spacer unit 10 is also the same as that described in the first embodiment. The difference with the second embodiment lies in the means of actuating the pressurized dispensing container 30.

As in the second embodiment, the cylindrical housing 36 is divided into upper and lower sections 65 and 66 by a partition having airflow holes 60.

The valve stem 63 of the pressurized dispensing container 30 is received sealingly in a tubular actuator 80 which defines an annular shoulder which acts as a stop limiting the extent to which the valve stem 63 extends within the actuator 80.

The actuator 80 is received as a snug fit within a downwardly extending tubular projection 81 formed integrally with the cylindrical housing 36. The tubular projection 81 has a lower end wall 94 defining an aperture 95 communicating with an annular space 96 formed between the lower end wall and the actuator 80. A nozzle 97 defined by the tubular projection 81 communicates with the annular space 96 and is orientated to release product from the annular space into the lower section 66 in the direction of the aperture 67 into the spacer chamber 11a.

A secondary valve means is formed in the tubular projection 81 by an annular valve seat 99 at the lower end of the actuator 80 and a resilient valve member 90 which extends from the lower section 66 into the annular space 96 and is normally urged into sealing contact with the valve seat 99 by a spigot 91. The valve member 90 has a cylindrical body which is recessed to accommodate the spigot 91 as an interference fit so that the spigot and valve member are sufficiently firmly connected to enable the valve member to be positively unseated from the valve seat when the spigot is retracted. The valve member is a sliding fit within the aperture 95 and is provided with a radially projecting flange 107 of greater diameter than the aperture 95 so that the flange acts as a stop limiting downward motion of the valve member 90 through the aperture.

The actuator 80 is provided with a radially extending flange 82 of external diameter slightly less than the internal diameter of the cylindrical housing 36 such that a restricted annular air passageway is defined between the flange 82 and the housing 36.

The actuator 80 and the hollow tubular valve stem together define a first chamber which is normally closed at its upper end by the internal valve means of the pressurized dispensing container and at its lower end by the secondary valve means.

In use, the user depresses the pressurized dispensing container 30 relative to the housing 36 so as to actuate the pressurized dispensing container 30 by relative movement between the container and the valve stem 63 which is prevented from downward movement by abutment with the annular shoulder in the actuator 80.

Actuation of the pressurized dispensing container 30 results in a pressurized metered dose of fluid entering the first chamber from which it is prevented from escaping by the secondary valve means. The user then inhales through the mouthpiece 12 thereby reducing air pressure within the spacer chamber 11a and the lower section 66 of the cylindrical housing 36. The annular flange 82 is subject to a downward force because of an imbalance of air pressure above and below the flange, since the air pressure above the flange is maintained at ambient air pressure by the airflow holes which are open to atmosphere. The flange 82 is thereby urged downwardly against the spring pressure provided by the spring. As the flange moves downwardly, the spigot 91 also moves downwardly thereby unseating the resilient valve member 90 from the valve seat 99 so that the pressurized fluid escapes from the first chamber into the annular space 96 which constitutes a second chamber. As fluid begins to escape, dissolved propellant in liquid form boils off from the dispensed dose causing the fluid to rapidly expand. This expansion assists in further displacing the valve member 90 away from the seal 99. Displacement of the valve member 90 away from the seat 99 is limited by engagement between the flange 107 and the lower end wall 94 of the tubular projection 81. The pressurized fluid in the second chamber, i.e., annular space 96, then escapes via the nozzle, and is drawn into the spacer chamber 11a.

The spacer chamber 11a imparts a cyclonic action to the dispensed product as described in the previous embodiments with the same beneficial results of classification of the aerosol droplets and slowing of the droplets.

It should be noted that the dispensing apparatus is suitable for use with other dispensing units which comprise means for actuating the pressurized dispensing container by the inhalation force produced by the user and is not restricted to the specific embodiment described herein.

A fourth embodiment of dispensing apparatus according to the present invention comprises the dispensing unit 30 and spacer unit 10 of the third embodiment. However, in addition, the dispensing apparatus is provided with a counter module 50 as described in the second embodiment.

What is claimed is:

1. Inhalation apparatus comprising a housing defining a socket for receiving a pressurized dispensing container, actuator means for receiving a valve stem of the pressurized dispensing container and a cylindrical chamber having an inlet located at a periphery of the chamber and an outlet at or near a center of the chamber, the actuator means defining duct means to direct product dispensed from the valve stem of the pressurized dispensing container through the inlet of the cylindrical chamber in a direction substantially tangential to a major axis of the cylindrical chamber, the outlet of the cylindrical chamber communicating with a mouthpiece, such that inhalation by a user on the mouthpiece creates a cyclonic airflow in the cylindrical chamber between the inlet and outlet in which the dispensed product is entrained for inhalation.

2. Inhalation apparatus as claimed in claim 1, wherein the width of the chamber, as measured in the direction of the major axis of the cylindrical chamber, decreases from the periphery of the chamber to the center.

3. Inhalation apparatus as claimed in claim 1, wherein an aperture is formed at or near the center on one side of the cylindrical chamber.

4. Inhalation apparatus as claimed in claim 1, wherein the socket comprises an upper section separated by a partition from a lower section which communicates with the inlet to the cylindrical chamber, airflow holes being provided in the partition.

5. Inhalation apparatus as claimed in claim 1, wherein the actuator means is actuated by inhalation of the user on the mouthpiece.

6. Inhalation apparatus as claimed in claim 1, wherein the actuation of the actuator means is co-ordinated with inhalation of the user on the mouthpiece.

7. Inhalation apparatus as claimed in claim 1 further comprising means for counting the number of actuations of the dispensing unit and displaying a visual indicator correlated to the number of actuations.

8. Inhalation apparatus as claimed in claim 7, wherein the visual indicator is a number indicating the number of actuations.

9. Inhalation apparatus as claimed in claim 7, wherein the visual indicator is a number indicating the number of actuations remaining before the pressurised dispensing container is empty.

10. Inhalation apparatus as claimed in claim 1 formed as a unitary moulding.

11. Inhalation apparatus as claimed in claim 1 wherein said chamber has a first side and a second side spaced apart along the major axis, with said first side having an aperture defining the outlet of the cylindrical chamber in communication with said mouthpiece.

12. Inhalation apparatus as claimed in claim 11 wherein said mouthpiece conmunicates with the outlet through a mouthpiece duct extending radially out from the outlet along said first side.

13. Inhalation apparatus as claimed in claim 12 wherein said mouthpiece duct is integrally formed with the first side of said chamber as to form a single unit.

14. Inhalation apparatus as claimed in claim 12 wherein said socket is a housing positioned on the second side of said chamber.

15. Inhalation apparatus as claimed in claim 14 wherein said housing is a cylindrical housing integrally formed with the second side of said chamber.

16. Inhalation apparatus as claimed in claim 11 wherein said socket is a housing positioned on the second side of said chamber.

17. Inhalation apparatus as claimed in claim 16 wherein said housing is a cylindrical housing integrally formed with the second side of said chamber.

18. A method of inhaling product dispensed from a pressurized dispensing container comprising the steps of inhaling on a mouthpiece of an inhalation apparatus comprising a cylindrical chamber having an inlet at a periphery thereof and an outlet at or near a center thereof which communicates with the mouthpiece, to thereby create a cyclonic airflow from the inlet to the outlet, actuating the pressurized dispensing container to dispense a dose of product through the inlet of the cylindrical chamber in a direction substantially tangential to a major axis of the cylindrical chamber such that the product is entrained in the airflow and inhaled through the mouthpiece.

19. A method as claimed in claim 18 wherein inhalation on the mouthpiece actuates the pressurized dispensing apparatus.

20. A method as claimed in claim 18 wherein said chamber has a first side and a second side spaced apart along the major axis, and the outlet being provided in the first side and wherein the product exits the chamber through the outlet while traveling in a common direction as the major axis and is redirected by a mouthpiece duct to travel radially along the first side of the chamber to a mouthpiece outlet.

* * * * *